(12) United States Patent
Grosch et al.

(10) Patent No.: US 6,491,861 B1
(45) Date of Patent: Dec. 10, 2002

(54) PROCESS FOR PRODUCTION OF A ZEOLITE-CONTAINING MOLDING

(75) Inventors: Georg Heinrich Grosch, Bad Dürkheim (DE); Ulrich Müller, Neustadt (DE); Andreas Walch, Heidelberg (DE); Norbert Rieber, Mannheim (DE); Wolfgang Harder, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,857

(22) PCT Filed: Jun. 5, 1998

(86) PCT No.: PCT/EP98/03394

§ 371 (c)(1),
(2), (4) Date: Dec. 6, 1999

(87) PCT Pub. No.: WO98/55229

PCT Pub. Date: Dec. 10, 1998

(30) Foreign Application Priority Data

Jun. 6, 1997 (DE) .......................................... 19723751

(51) Int. Cl.[7] .................................................. B28B 3/20
(52) U.S. Cl. ........................ 264/628; 264/638; 264/656
(58) Field of Search ................................ 264/628, 638, 264/656

(56) References Cited

U.S. PATENT DOCUMENTS 5,387,564 A * 2/1995 Takeuchi et al. .............. 502/62
5,430,000 A   7/1995 Timken ....................... 502/60

FOREIGN PATENT DOCUMENTS

| CA | 2256383 | 12/1997 |
|---|---|---|
| DE | 196 23 609 | 12/1997 |
| DE | 196 23 611 | 12/1997 |
| EP | 0 102 544 | 3/1984 |
| EP | 0 592 050 | 4/1994 |
| WO | WO 94/13584 | 6/1994 |
| WO | WO 94/29408 | 12/1994 |

OTHER PUBLICATIONS

Derwent Abstracts, AN 91–091645/13, JP 03–037156, Feb. 18, 1991.

* cited by examiner

*Primary Examiner*—Christopher A. Fiorilla
(74) *Attorney, Agent, or Firm*—Oblon, Spivak, McClelland, Maier & Neustadt, P.C.

(57) ABSTRACT

A process for the production of a molding containing at least one zeolite, wherein the at least one zeolite contains a titanium-, zirconium-, chromium-, niobium-, iron- or vanadium-containing zeolite:

(I) adding a mixture consisting of at least one alcohol selected from the group consisting of methanol, ethanol, propanol or butanol, and water to a mixture containing said zeolite or a mixture of two or more thereof, and (II) kneading, molding, drying and calcining the mixture from (I);

wherein the molding is useful as a catalyst, particularly in epoxidation reactions.

8 Claims, No Drawings

PROCESS FOR PRODUCTION OF A ZEOLITE-CONTAINING MOLDING

This application is a 371 of PCT/EP 98/03394 filed Jun. 5, 1998.

BACKGROUND OF THE INVENTION

1. Field of the Invention

The present invention relates to a molding containing at least one porous oxidic material, a process for its production, and its use for the reaction of organic compounds, in particular for the epoxidation of organic compounds having at least one C—C double bond. The molding described herein has high abrasion resistance and excellent mechanical properties.

2. Description of the Background

Abrasion-resistant moldings comprising catalytically active materials are employed in many chemical processes, in particular in processes using a fixed bed. Accordingly, there is a huge wealth of literature on this subject. There is significantly less literature on the use of catalysts based on porous oxidic materials, for example zeolites, and especially relating to the molding of such materials.

For the production of solids, a binder, an organic viscosity-enhancing compound and a liquid for converting the material into a paste are generally added to the catalytically active material, ie. the porous oxidic material, and the mixture is compacted in a mixing or kneading apparatus or an extruder. The resulting plastic material is then molded, in particular using an extrusion press or an extruder, and the resulting moldings are dried and calcined.

A number of inorganic compounds are used as binders.

For example, according to US-A 5,430,000, titanium dioxide or hydrated titanium dioxide is used as the binder. Examples of further prior art binders are:

hydrated alumina or other aluminum-containing binders (WO 94/29408);

mixtures of silicon and aluminum compounds (WO 94/13584);

silicon compounds (EP-A 0 592 050);

clay minerals (JP-A 03 037 156);

alkoxysilanes (EP-B 0 102 544).

The organic viscosity-enhancing substances used are generally hydrophilic polymers, eg. cellulose or polyacrylates.

The Applicant itself, in DE-A 196 23 611.8, furthermore describes an oxidation catalyst having a zeolite structure and molded by compacting shaping processes, and its use in the preparation of epoxides from olefins and hydrogen epoxide, and, in DE-A 196 23 609.6, an oxidation catalyst which is based on titanium or vanadium silicalites having the zeolite structure and which has likewise been molded by compacting shaping processes and contains from 0.01 to 30% by weight of one or more noble metals as defined therein.

In all publications according to the prior art cited above, water is used in the preparation of the moldings described there, as a liquid for converting the material into a paste (pasting agent).

However, the moldings described above and based on a porous oxidic material, for example zeolites and in particular titanium silicalites, have several disadvantages. Thus many of the moldings described in the above literature have insufficient mechanical strength for use as a catalyst in a fixed bed.

This is particularly important when secondary reactions of certain binders are undesirable and for this reason whole classes of binders which can impart sufficient strength to such a molding cannot be used, for example because of other adverse properties. For example, aluminum-containing binders cannot be used in the preparation of titanium silicalite which is used as a catalyst for the epoxidation of, for example, propylene with hydrogen peroxide, since the acidity induced by the aluminum-containing binder results in a greater degree of ring cleavage and formation of by-products. Moreover, titanium-containing binders can lead to high decomposition rates of the hydrogen peroxide used if these titanium-containing binders result in detectable titanium dioxide contents in the molding.

It is also undesirable to use binders which contain >100 ppm of alkali metals or alkaline earth metals. By using such binders, the catalytic activity of, for example, titanium silicalite can be severely adversely affected since the catalytically active Ti centers are inactivated by the alkali metal or alkaline earth metal ions.

SUMMARY OF THE INVENTION

It is thus an object of the present invention to provide a molding which contains at least one porous oxidic material and has sufficient mechanical stability to be used as a catalyst in a fixed bed. When it is used for catalytic reactions, the activity or selectivity losses due to secondary reactions of the added binder should be avoided in comparison with the prior art catalysts. A process for its production is also provided.

We have found surprisingly, that this object is achieved and, a molding which contains at least one porous oxidic material and exhibits virtually no activity and selectivity losses, or none at all, when used as a catalyst can be obtained if a mixture containing at least one alcohol and water is used as a pasting agent in its production.

Further improved moldings of the type under discussion here are obtained if a metal acid ester or a mixture of two or more thereof is used as the binder in addition to the pasting agent defined above.

DETAILED DESCRIPTION OF THE INVENTION

Accordingly, the present invention relates to a molding containing at least one porous oxidic material and obtainable by a process which comprises the following stages:

(I) addition of a mixture containing at least one alcohol and water to a mixture containing a porous oxidic material or a mixture of two or more thereof and (II) kneading, molding, drying and calcination of the mixture according to stage (I) after addition, and a process for the production of a molding containing at least one porous oxidic material, which comprises the following stages:

(I) addition of a mixture containing at least one alcohol and water to a mixture containing a porous oxidic material or a mixture of two or more thereof, and (II) kneading, molding, drying and calcination of the mixture according to stage (I) after addition.

The novel preparation of the moldings described above starting from a porous oxidic material in powder form comprises the formation of a plastic material which contains at least one porous oxidic material, a binder, a mixture containing at least one alcohol and water, if required one or more organic viscosity-enhancing substances and further prior art additives.

The plastic material obtained by thorough mixing, in particular kneading, of the above components is preferably molded by means of extrusion pressing or extruding and the resulting molding is then dried and finally calcined.

There are no particular restrictions with regard to the porous oxidic materials which may be used for the production of the novel molding, as long as it is possible to prepare a molding as described herein starting from these materials.

The porous oxidic material is preferably a zeolite, particularly preferably a titanium-, zirconium-, chromium-, niobium-, iron- or vanadium-containing zeolite, in particular a titanium silicalite.

Zeolites are known to be crystalline aluminosilicates having ordered channel and cage structures which have micropores. The term micropores as used in the present invention corresponds to the definition in Pure Appl. Chem. 45 (1976), p. 71 et seq., in particular p. 79, and denotes pores having a diameter of less than 2 nm. The network of such zeolites is composed of $SiO_4$ and $AlO_4$ tetrahedra which are linked via common oxygen bridges. An overview of the known structures is given, for example, by W. M. Meier and D. H. Olson in the Atlas of Zeolite Structure Types, Elsevier, 4th Edition, London 1996.

There are also zeolites which contain no aluminum and in which some of the Si(IV) has been replaced by titanium as Ti(IV) in the silicate lattice. The titanium zeolites, in particular those having a crystal structure of the MFI type, and possibilities for their preparation are described, for example in EP-A 0 311 983 or EP-A 0 405 978. Apart from silicone and titanium, such materials can also contain additional elements, such as aluminum, zirconium, tin, iron, cobalt, nickel, gallium, boron or small amounts of fluorine.

In the zeolites described, some or all of the titanium itself therein may be replaced by vanadium, zirconium, chromium, niobium or iron. The molar ratio of titanium and/or vanadium, zirconium, chromium, niobium or iron to the sum of silicon and titanium and/or vanadium, zirconium, chromium, niobium or iron is generally from 0.01:1 to 0.1:1.

Titanium zeolites having the MFI structure are known to be identifiable by a certain pattern in their X-ray diffraction photographs and additionally by a structural vibration band in the infrared region (IR) at about 960 $cm^{-1}$ and thus differ from alkali metal titanates or crystalline and amorphous $TiO_2$ phases.

Usually, the stated titanium, zirconium, chromium, niobium, iron and vanadium zeolites are prepared by reacting an aqueous mixture comprising an $SiO_2$ source, a titanium, zirconium, chromium, niobium, iron or vanadium source, for example titanium dioxide or a corresponding vanadium oxide, zirconium alcoholate, chromium oxide, niobium oxide or iron oxide, and a nitrogen-containing organic base as a template, eg. tetrapropylammonium hydroxide, if necessary also with the addition of basic compounds, in a pressure-resistant container at elevated temperature for several hours or a few days, a crystalline product being formed. This is filtered off, washed, dried and subjected to combustion at elevated temperatures to remove the organic nitrogen base. In the powder thus obtained, some or all of the titanium or of the zirconium, chromium, niobium, iron and/or vanadium is present within the zeolite structure in varying amounts with 4-, 5- or 6-fold coordination. To improve the catalytic behavior, repeated washing with hydrogen peroxide solution containing sulfuric acid may also be carried out subsequently, after which the titanium or zirconium, chromium, niobium, iron or vanadium zeolite powder must once again be dried and subjected to combustion; this may be followed by a treatment with alkali metal compounds in order to convert the zeolite from the H form into the cationic form. The titanium or zirconium, chromium, niobium, iron or vanadium zeolite powder prepared in this manner is then processed to give a molding as described below.

Preferred zeolites are titanium, zirconium, chromium, niobium or vanadium zeolites, particularly preferably those having a pentasil zeolite structure, in particular the types assigned by X-ray analysis to the BEA, MOR, TON, MTW, FER, MFI, MEL, CHA, ERI, RHO, GIS, BOG, NON, EMT, HEU, KFI, FAU, DDR, MTT, RUT, LTL, MAZ, GME, NES, OFF, SGT, EUO, MFS, MCM-22 or MFI/MEL mixed structure. Zeolites of this type are described, for example, in the abovementioned publication by Meier and Olson. Titanium-containing zeolites having the UDT-1, CIT-1, CIT-S, ZSM48, MCM-48, ZSM-12, ferrierite, β-zeolite or mordenite structure are also possible for the present invention. Such zeolites are described, inter alia, in US-A 5 430 000 and WO 94/29408, the content of which in this context is fully incorporated by reference in the present Application.

There are also no particular restrictions with regard to the pore structure of the novel moldings, ie. the novel molding may have micropores, mesopores, macropores, micro- and mesopores, micro- and macropores or micro-, meso- and macropores, the definition of the terms mesopores and macropores likewise corresponding to those in the abovementioned literature according to Pure Appl. Chem. and denoting pores having a diameter of from >2 nm to about 50 nm and > about 50 nm, respectively.

Furthermore, the novel molding may be a material based on a mesoporous silicon-containing oxide and a silicon-containing xerogel.

Silicon-containing mesoporous oxides which also contain Ti, V, Zr, Sn, Cr, Nb or Fe, in particular Ti, V, Zr, Cr, Nb or a mixture of two or more thereof, are particularly preferred.

Suitable binders are in principle all compounds used to date for such purposes. Compounds, in particular oxides, of silicon, of aluminum, of boron, of phosphorus, of zirconium and/or of titanium are preferably used. Of particular interest as a binder is silica, where the $SiO_2$ may be introduced into the shaping step as a silica sol or in the form of tetraalkoxysilanes. Oxides of magnesium and of beryllium and clays, for example montmorillonites, kaolins, bentonites, halloysites, dickites, nacrites and anauxites, may furthermore be used as binders.

However, a metal acid ester or a mixture of two or more thereof is preferably added as a binder in stage (I) of the novel process. Particular examples of these are orthosilicic esters, trialkoxysilanes, tetraalkoxytitanates, trialkoxyaluminates, tetraalkoxyzirconates and a mixture of two or more thereof.

However, tetraalkoxysilanes are particularly preferably used as binders in the present invention. Specific examples are tetramethoxysilane, tetraethoxysilane, tetrapropoxysilane and tetrabutoxysilane, the analogous tetraalkoxytitanium and tetraalkoxyzirconium compounds and trimethoxy-, triethoxy-, tripropoxy- and tributoxyaluminum, tetramethoxysilane and tetraethoxysilane being particularly preferred.

The novel molding preferably contains up to about 80, particularly preferably from about 1 to about 50, % by weight in particular from about 3 to about 30, % by weight, of the binder, in each case based on the total mass of the molding, the binder content being calculated from the amount of metal oxide formed.

The metal acid ester preferably used is employed in an amount such that the resulting metal oxide content in the molding is from about 1 to about 80, % by weight, preferably from about 2 to about 50, % by weight, in particular from about 3 to about 30, % by weight, based on the total mass of the molding.

As is already evident from the above, mixtures of two or more of the abovementioned binders may of course also be employed.

It is essential for the present invention that a mixture containing at least one alcohol and water is used as a pasting agent in the production of the novel molding. The alcohol content of this mixture is in general from about 1 to about 80, % by weight, preferably from about 5 to about 70, % by weight, in particular from about 10 to about 60, % by weight, in each case based on the total weight of the mixture.

The alcohol used preferably corresponds to the alcohol component of the metal acid ester preferably used as the binder, but it is also not critical to use another alcohol.

There are no restrictions at all with regard to the alcohols which may be used, provided that they are water-miscible. Accordingly, both monoalcohols of 1 to 4 carbon atoms and water-miscible polyhydric alcohols may be used. In particular, methanol, ethanol, propanol, n-butanol, isobutanol, tert-butanol and mixtures of two or more thereof are used.

The organic viscosity-enhancing substance used may likewise be any prior art substances suitable for this purpose. Those preferred are organic, in particular hydrophilic polymers, eg. cellulose, starch, polyacrylates, polymethacrylates, polyvinyl alcohol, polyvinylpyrrolidone, polyisobutene and polytetrahydrofuran. These substances primarily promote the formation of a plastic material during the kneading, molding and drying step by bridging the primary particles and moreover ensuring the mechanical stability of the molding during the molding and drying process. These substances are removed from the molding during calcination.

Amines or amine-like compounds, for example tetraalkylammonium compounds or aminoalcohols, and carbonate-containing substances, such as calcium carbonate, may be used as further additives. Such further additives are described in EP-A 0 389 041, EP-A 0 200 260 and WO 95/19222, which are incorporated fully by reference in the context of the present Application.

Instead of basic additives, it is also possible to use acidic additives. These can effect, inter alia, a more rapid reaction of the metal acid ester with the porous oxidic material. Organic acidic compounds which can be burnt out by calcination after the molding step are preferred. Carboxylic acids are particularly preferred. It is of course also possible to incorporate mixtures of two or more of the abovementioned additives.

The order of addition of the components of the material containing the porous oxidic material is not critical. It is possible either to add first the binder, then the organic viscosity-enhancing substance and, if required, the additive and finally the mixture containing at least one alcohol and water or to interchange the order with respect to the binder, the organic viscosity-enhancing substance and the additives.

After the addition of the binder to the porous oxide powder, to which the organic viscosity-enhancing substance may already have been added, the generally still pulverulent material is homogenized for from 10 to 180 minutes in a kneader or extruder. As a rule, temperatures of from about 10° C. to the boiling point of the pasting agent and atmospheric or slightly superatmospheric pressure are employed. The remaining components are then added, and the mixture thus obtained is kneaded until a plastic material capable of being molded in an extrusion press or extruder is formed.

In principle, the kneading and the molding can be effected using all conventional kneading and molding apparatuses or methods, many of which are disclosed in the As already indicated, however, preferred processes are those in which molding is effected by extrusion in conventional extruders, for example to give extrudates having a diameter of, usually, from about 1 to about 10 mm, in particular from about 2 to about 5 mm. Such extrusion apparatuses are described, for example, in Ullmann's Enzylopädie der Technischen Chemie, 4th Edition, Vol. 2, p. 295 et seq., 1972. In addition to the use of an extruder, an extrusion press is preferably also used for molding.

After the end of the extrusion pressing or extruding, the resulting moldings are dried at, in general, from about 30 to 140° C. (for from 1 to 20 hours at atmospheric pressure) and calcined at from about 400 to about 800° C. (for from 3 to 10 hours at atmospheric pressure).

The resulting moldings or extrudates can of course be comminuted. They are preferably comminuted to give granules or chips having a particle diameter of from 0.1 to 5 mm, in particular from 0.5 to 2 mm.

These granules or these chips and also moldings produced by another method contain virtually no fractions and particles finer than those with a minimum particle diameter of about 0.1 mm.

The moldings according to the invention containing a porous oxidic material or produced by the novel process have improved mechanical stability while at the same time retaining the activity and selectivity in comparison with corresponding prior art moldings.

The moldings according to the invention or produced according to the invention can be employed for the catalytic conversion of organic molecules. Reactions of this type are, for example, oxidations, the epoxidation of olefins, for example the preparation of propylene oxide from propylene and $H_2O_2$, the hydroxylation of aromatics, for example hydroquinone from phenol and $H_2O_2$, the conversion of alkanes into alcohols, aldehydes and acids, isomerization reactions, for example the conversion of epoxides into aldehydes, and further reactions described in the literature with such moldings, in particular zeolite catalysts, as described, for example, in W. Hölderich, Zeolites: Catalysts for the Synthesis of Organic Compounds, Elsevier, Stud. Surf. Sci. Catal., 49, Amsterdam (1989), pp. 69 to 93, and, in particular for possible oxidation reactions, by B. Notari in Stud. Surf. Sci. Catal., 37 (1987), 413 to 425.

The zeolites discussed in detail above are particularly suitable for the epoxidation of olefins, preferably those of 2 to 8 carbon atoms, particularly preferably ethylene, propylene or butene, in particular propene, to give the corresponding olefin oxides. Accordingly, the present invention relates in particular to the use of the molding described herein for the preparation of propylene oxide starting from propylene and hydrogen peroxide.

The present invention in its most general embodiment moreover relates to the use of a mixture containing at least one alcohol and water as a pasting agent, preferably in combination with a metal acid ester as a binder, for the preparation of moldable mixtures which contain at least one porous oxidic material.

EXAMPLES

Example 1

910 g of tetraethyl orthosilicate were initially taken in a 4 l four-necked flask and 15 g of tetraisopropyl orthotitanate were added from a dropping funnel in the course of 30 minutes while stirring (250 rpm, paddle stirrer). A colorless, clear mixture formed. 1600 g of a 20% strength by weight tetrapropylammonium hydroxide solution (alkali metal content <10 ppm) were then added and stirring was continued for a further hour. The alcohol mixture (about 900 g) formed from the hydrolysis was distilled off at from 90 to 100° C. The mixture was made up with 3 l of water and the meanwhile slightly opaque sol was transferred to a 5 l stainless steel stirred autoclave.

The closed autoclave (anchor stirrer, 200 rpm) was brought to a reaction temperature of 175° C. at a heating rate of 3° C./min. The reaction was complete after 92 hours. The cooled reaction mixture (white suspension) was centrifuged and the sediment was washed several times with water until it was neutral. The solid obtained was dried at 110° C. in the course of 24 hours (weight obtained 298 g).

The template remaining in the zeolite was then burnt off under air at 550° C. in 5 hours (calcination loss: 14% by weight).

According to wet chemical analysis, the pure white product had a Ti content of 1.5% by weight and a residual alkali content of less than 100 ppm. The yield was 97%, based on $SiO_2$ used. The crystallites had a size of from 0.05 to 0.25 μm and the product showed a typical band at about 960 $cm^{-1}$ in the IR.

Example 2

120 g of titanium silicalite powder, synthesized according to Example 1, were mixed with 48 g of tetramethoxysilane for 2 h in a kneader. 6 g of Walocel (methylcellulose) were then added. For conversion into a paste, 77 ml of a water/methanol mixture containing 25% by weight of methanol were then added. The material obtained was compacted for a further 2 h in the kneader and then molded in an extrusion press to give 2 mm moldings. The moldings obtained were dried at 120° C. for 16 h and then calcined at 500° C. for 5 h. The lateral compressive strength of the resulting moldings was tested. The lateral compressive strength was 4.11 kg. 10 g of the moldings thus obtained were processed to give chips (particle size 1–2 mm) and used as catalyst A in the epoxidation of propene with hydrogen peroxide.

Comparative Example 1

120 g of titanium silicalite powder, synthesized according to Example 1, were mixed with 48 g of tetramethoxysilane for 2 h in a kneader. 6 g of Walocel (methylcellulose) were then added. For conversion into a paste, 80 ml of water were then added. The material obtained was compacted for a further 2 h in the kneader and then molded in an extrusion press to give 2 mm moldings. The moldings obtained were dried at 120° C. for 16 h and then calcined at 500° C. for 5 h. The lateral compressive strength of the resulting moldings was tested. The lateral compressive strength was 3.59 kg. 10 g of the moldings thus obtained were processed to give chips (particle size 1–2 mm) and used as catalyst B in the epoxidation of propene with hydrogen peroxide.

Example 3

120 g of titanium silicalite powder, synthesized according to Example 1, were dry-blended with 6 g of Walocel (methylcellulose) and mixed with 48 g of tetraethoxysilane for 30 min. in a kneader. For conversion into a paste, 75 ml of a water/ethanol mixture containing 50% by weight of ethanol were then added. The material obtained was compacted for a further 1 h in the kneader and then molded in an extrusion press to give 2 mm moldings. The moldings obtained were dried at 120° C. for 16 h and then calcined at 500° C. for 5 h. The lateral compressive strength of the resulting moldings was tested. The lateral compressive strength was 3.08 kg. 10 g of the moldings thus obtained were processed to give chips (particle size 1–2 mm) and used as catalyst C in the epoxidation of propene with hydrogen peroxide.

Comparative Example 2

120 g of titanium silicalite powder, synthesized according to Example 1, were mixed with 48 g of tetraethoxysilane for 2 h in a kneader. 6 g of Walocel (methylcellulose) were then added. For conversion into a paste, 79 ml of water were then added. The material obtained was compacted for a further 1 h in the kneader and then molded in an extrusion press to give 2 mm moldings. The moldings obtained were dried at 120° C. for 16 h and then calcined at 500° C. for 5 h. The lateral compressive strength of the resulting moldings was tested. The lateral compressive strength was 1.92 kg. 10 g of the moldings thus obtained were processed to give chips (particle size 1–2 mm) and used as catalyst D in the epoxidation of propene with hydrogen peroxide.

Comparative Example 3

120 g of titanium silicalite powder, synthesized according to Example 1, were compacted with 6 g of Walocel (methylcellulose), 30 g of silica sol (Ludox AS-40) and 85 ml of water for 2 h in a kneader. The material thus obtained was then molded in an extrusion press to give 2 mm moldings. The moldings obtained were dried at 120° C. for 16 h and then calcined at 500° C. for 5 h. The lateral compressive strength of the resulting moldings was tested. The lateral compressive strength was 0.89 kg. 10 g of the moldings thus obtained were processed to give chips (particle size 1–2 mm) and used as catalyst E in the epoxidation of propene with hydrogen peroxide.

Examples 4 to 8

Catalysts A to E were installed in a steel autoclave with basket insert and gassing stirrer in each case in an amount in grams such that the weight of installed titanium silicalite was 0.5 g. The autoclave was filled with 100 g of methanol, closed and tested for leakage. It was then heated to 40° C., and 11 g of liquid propene were metered into the autoclave. 9.0 g of an aqueous hydrogen peroxide solution (hydrogen peroxide content of the solution 30% by weight) were then pumped into the autoclave by means of an HPLC pump, and the hydrogen peroxide residues in the feed lines were then flushed into the autoclave by means of 16 ml of methanol. The initial hydrogen peroxide content of the reaction solution was 2.5% by weight. After a reaction time of 2 h, the autoclave was cooled and its pressure let down. The liquid discharge was investigated cerimetrically for hydrogen peroxide. The analysis and the determination of the propylene oxide content were carried out by gas chromatography.

| Catalyst | Propylene oxide content (% by weight) | Residual hydrogen peroxide content (% by weight) |
|---|---|---|
| A | 1.42 | 0.99 |
| B (comparison) | 1.19 | 1.12 |
| C | 1.28 | 1.10 |
| D (comparison) | 1.15 | 1.20 |
| E (comparison) | 1.49 | 0.98 |

What is claimed is:

1. A process for the production of a molding containing at least one zeolite, wherein the at least one zeolite contains a titanium-, zirconium-, chromium-, niobium-, iron- or vanadium-containing zeolite, comprising:

(1) adding a mixture consisting of at least one alcohol selected from the group consisting of methanol, ethanol, propanol and butanol, and water to a mixture containing said zeolite or a mixture of two or more thereof, and (II) kneading, molding, drying and calcining the mixture from (I), wherein a binder is additionally added to the mixture in (I).

2. The process as claimed in claim 1, wherein at least one zeolite contains a titanium silicalite.

3. The process as claimed in claim 1, wherein the binder comprises a metal acid ester or a mixture of two or more thereof.

4. The process as claimed in claim 3, wherein the metal acid ester is selected from the group consisting of an orthosilicic ester, a tetraalkoxysilane, a tetraalkoxytitanate, a trialkoxyaluminate, a tetraalkoxyzirconate and a mixture of two or more thereof.

5. The process as claimed in claim 4, wherein the alcohol in the mixture consisting of at least one alcohol and water corresponds to the alcohol in the metal acid ester.

6. The process as claimed in claim 1, wherein an organic hydrophilic polymer or a mixture of two or more thereof is additionally added to the mixture in (I).

7. The process as claimed in claim 1, wherein the mixture obtained in (I) is molded by extrusion pressing or extruding.

8. The process as claimed in claim 1, wherein the molding containing at least one zeolite has micropores, mesopores, macropores, micro- and macropores or micro-, meso- and macropores.

* * * * *